US00PP16162P3

(12) United States Plant Patent
Diboll

(10) Patent No.: US PP16,162 P3
(45) Date of Patent: Dec. 13, 2005

(54) ***ANDROPOGON* PLANT NAMED 'BIG DADDY'**

(50) Latin Name: *Andropogon gerardi*
Varietal Denomination: Big Daddy

(76) Inventor: Neil Hart Diboll, P.O. Box 306, Westfield, WI (US) 53964-0306

( * ) Notice: Subject to any disclaimer, the term of this patent is extended or adjusted under 35 U.S.C. 154(b) by 102 days.

(21) Appl. No.: 10/799,202

(22) Filed: Mar. 12, 2004

(65) Prior Publication Data

US 2005/0204445 P1 Sep. 15, 2005

(51) Int. Cl.[7] ..... A01H 5/00

(52) U.S. Cl. ..... Plt./384

(58) Field of Search ..... Plt./384

*Primary Examiner*—Anne Marie Grunberg
(74) *Attorney, Agent, or Firm*—Penny J. Aguirre

(57) ABSTRACT

A new cultivar of Big bluestem, *Andropogon gerardi* 'Big Daddy', that is characterized by its clump-forming growth habit, its sturdy and upright plant habit, and its dense seen heads that are deep reddish purple in color.

2 Drawing Sheets

Botanical classification: *Andropogon gerardi.*
Varietal designation: 'Big Daddy'.

BACKGROUND OF THE INVENTION

The present invention relates to a new and distinct cultivar of *Andropogon gerardi* and will be referred to hereafter by its cultivar name, 'Big Daddy'. 'Big Daddy' represents a new cultivar of Big bluestem, an ornamental grass grown for landscape use.

The inventor discovered and selected the new cultivar, 'Big Daddy', in a cultivated field in Westfield, Wis. in the fall of 1997. 'Big Daddy' was discovered as a naturally occurring variant seedling in a cultivated field sown for seed production. The seeds sown were collected from unnamed plants of *Andropogon gerardi,* therefore, 'Big Daddy' is a variant of the species and has no identifiable parents.

The new cultivar 'Big Daddy' was selected as unique because of its sturdy and upright plant habit, and its dense seed heads that are deep reddish purple in color.

Asexual reproduction of the new cultivar was first accomplished by culm division in Westfield, Wis. in the spring of 1999 by the inventor. The characteristics of this cultivar have been determined to be stable and are reproduced true to type in successive generations.

SUMMARY OF THE INVENTION

The following traits have been repeatedly observed and represent the characteristics of the new cultivar. 'Big Daddy' has not been observed under all possible environmental conditions. The phenotype may vary somewhat with variations in temperature, day-length, light intensity, soil types, and water and fertility levels without, however, any variance in genotype. The measurements, observations, and descriptions that follow describe plants grown outdoors in Westfield, Wis. These attributes in combination distinguish 'Big Daddy' from any selections of *Angropogon gerardi* known to the inventor.

1. The plant habit of 'Big Daddy' is sturdy and upright due to thicker culms than the species. The habit of the species is less erect, more open, and the culms tend to lodge as the seed heads mature.
2. The seed heads are more dense and mature to a deeper reddish purple color than is typical for the species.
3. The culm and foliage color of 'Big Daddy' is green during the summer with the culm color changing to a purple-red color as the plant matures in fall. In fall, the color effect of the sheathed culms is alternating green and purple-red.
4. 'Big Daddy' reaches a height of up to 1.8 to 2.5 m (6 to 8 ft) with a spread of about 20 cm (at base) in 2 years of growing time from a single division.
5. 'Big Daddy' is hardy in Zones 3 to 7.
6. 'Big Daddy' is tolerant to a wide range of soil types; growing well in moderately fertile well-drained and moist soils in full sun.

BRIEF DESCRIPTION OF THE DRAWING

The accompanying colored photographs illustrate the overall appearance and distinct characteristics of the new *Andropogon.*

The photograph in FIG. One illustrates the overall habit and appearance of 'Big Daddy' in October in Westfield, Wis. as grown outdoors for three years.

The photograph in FIG. Two is a close-up of the seed heads on the same plant.

FIG. Three is a photograph taken in August of a two-year old plant as grown in Plymouth, Minn. and represents the foliage and culm color of 'Big Daddy' in summer.

The colors in the photographs are as close as possible with the photographic and printing technology utilized. The color values cited in the detailed botanical description accurately describe the colors of the new *Miscanthus.*

DETAILED BOTANICAL DESCRIPTION

The following is a detailed description of the new cultivar as grown outdoors trial bed in Plymouth, Minn. for two years from a single division. The color determination is in accordance with the 2001 R.H.S. Colour Chart of The Royal Horticultural Society, London, England, except where general color terms of ordinary dictionary significance are used.

Botanical classification: 'Big Daddy' is a cultivar of *Andropogon gerardi.*

Common name: 'Big Daddy' Big bluestem.

Parentage: Naturally occurring mutant seedling of *Andropogon gerardi.*

General description:

*Blooming period.*—Blooms from late August through early September, 3 to 4 weeks.

*Plant habit.*—Herbaceous, clump-forming, ornamental grass with an upright habit, all culms arise from rhizomes (un-branched).

*Height and spread.*—Reaches up to 1.8 m (6 ft) in height with a spread of about 20 cm (at base) in 2 years of growing time from a single division.

*Hardiness.*—Zone 3 to 7.

*Culture.*—Grows best in moderately fertile, well-drained to moist soils in full sun.

*Diseases and pests.*—No susceptibility or resistance to diseases or pests that affect *Andropogon* has been observed.

*Root description.*—Deep rooted with fibrous roots from short rhizomes.

*Rhizome color.*—155D with diagonal ridges of 177D.

Growth and propagation:

*Propagation.*—Culm division, preferably in spring.

*Time required for root development from a single division.*—A single culm division planted in a bark-based media will fully develop roots in a one quart container in 3 to 4 months when grown outdoors under standard summer temperatures and natural lighting.

*Growth rate.*—Moderate.

Culm (stem) description:

*General.*—Round, robust, pithy, solid at nodes.

*Culm aspect.*—Rigid and held erect, lateral culms are held at an angle of about 20° from center, but culms do not lodge as is typical of the species.

*Branching.*—Un-branched.

*Culm color.*—Summer: unsheathed areas 182B to 182C (grey-red), sheathed areas 144A (green). Fall: Summer: unsheathed areas 184D to 184C (greyed purple), sheathed areas 146C (yellow-green).

*Culm size.*—About 3 to 5 mm (unsheathed) in width, up to 1.8 m (6 ft) in height.

*Culm surface.*—Glabrous (slightly lustrous).

*Internode length.*—About 10 to 16 cm (between leaf blade attachments).

*Ligule.*—Membranous, about 1 mm in width and 144A in color, can be glaucous.

Foliage description:

*Leaf arrangement.*—Alternate, 2 ranked.

*Leaf shape.*—Linear.

*Leaf division.*—Simple.

*Leaf base.*—Sheathed to next lower node, sheath surrounds about on half of culm at leaf attachment and completely surrounds at leaf attachment.

*Leaf apex.*—Attenuating to a fine tip.

*Leaf aspect.*—Leaf blades diverge from leaf sheath at about a 15 to 30° C. angle from center of culm and then cascade.

*Leaf venation.*—Parallel, not conspicuous, midrib is recessed upper surface and raised on lower surface. Veins impart a coarse appearance.

*Vein color.*—Upper surface: midrib color matches leaf color with secondary veins 137D, Lower surface: all veins match leaf color, only midrib is prominent.

*Leaf margins.*—Entire, scabrous.

*Leaf auricles.*—Not present.

*Leaf persistence.*—Foliage dries but is persistent throughout the winter.

*Leaf attachment.*—Sheathed. Leaves fully encircle the culm at the note to about ⅔ of the way up to the ligule, the top ⅓ of the sheath encircles about ½ of the culm. The ligule and leaf blade arise near the next distal node.

*Leaf bud arrangement.*—Curled.

*Leaf size.*—Leaf sheath is 10 to 16 cm in length, leaf blade is 18 to 50 cm in length and 1 to 1.5 cm in width tapering to a point at the apex.

*Leaf surface.*—Glabrous on upper surface and slightly glaucous on lower surface. Lower leaf blades and sheaths are villous.

*Leaf number.*—5 to 7 on a 1.5 m culm.

*Leaf color.*—Early summer: upper surface 146B, lower surface 146C. Early fall: upper surface 137B, lower surface 137C. Winter color 177D.

*Leaf fragrance.*—None.

*Peduncle description.*—10 to 15 cm in length, sheathed ¾ of proximal portion, 2 mm in width, 144A in color.

Flower description:

*General description.*—Inflorescence composed of 2 to 3-parted racemes arising from terminal and laterally on long-exserted peduncles from top 2 to 3 nodes. Racemes are composed of both sessile, perfect spikelets and pedicellate spikelets that are either staminate or sterile. Spikelets are arranged in pairs at each node of articulate rachis, one sessile and one pedicellate.

*Lastingness of inflorescence.*—Racemes are persistent from fall through winter.

*Fragrance.*—None.

*Raceme number.*—3 to 8 per stem, about 65 per 21 cm clump.

*Raceme color.*—Mixture of 137D (green), 59A (purple), and 166D (greyed-orange, glume color). Overall effect is reddish purple, most closely represented by N77D (purple).

*Raceme aspect.*—Racemes held upright with outward or pendant spikelets.

*Raceme size.*—5 to 8 cm in length, 2 to 3 cm in width.

*Spikelet size.*—7 to 12 mm in length, about 1.5 mm in width.

*Spikelet shape.*—Elliptical.

*Sessile spikelet description.*—Fertile, perfect, first glume is 7 mm in length, 1.5 mm in width, second glume is 1 cm in length and 1.5 mm in width, glumes are 166D in color, lemma and palae are 166D in color but translucent and smaller than glumes, the lemma has a single awn that is very fine and about 1.5 mm in length and whitish in color.

*Pedicillate spikelets.*—Similar to sessile spikelets but on 4 mm pedicel, lemma is awnless and they are sterile (occasionally staminate).

Reproductive organs:

*Androecium.*—Primarily present on sessile spikelets, 3 stamens, 4 mm in length and 1 mm in width, 59A in color. Pollen was not observed.

*Gynoecium.*—1 pistil, 2 stigmas, stigma is 2.5 mm in length and 0.5 mm in width, feathery, 202A in color. Ovary: superior, minute, not easily quantifiable in size and color.

*Caryopsis.*—Enclosed in glumes and lemma, 4 mm in length and 1.5 mm in width, 176C in color.

No apomictic reproduction is believed to occur with this species.

It is claimed:

1. A new and distinct cultivar of *Andropogon* plant named 'Big Daddy' as herein illustrated and described.

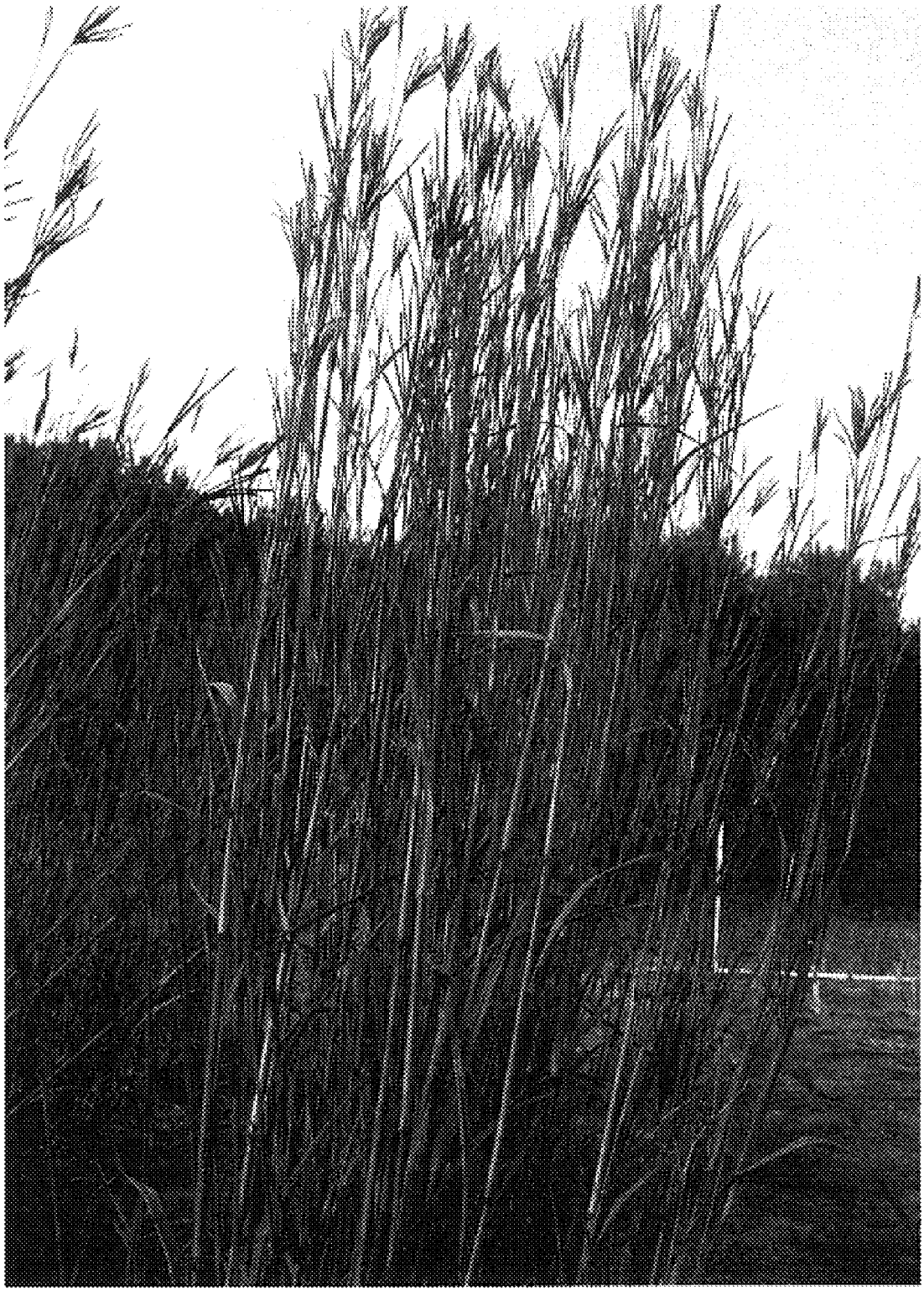

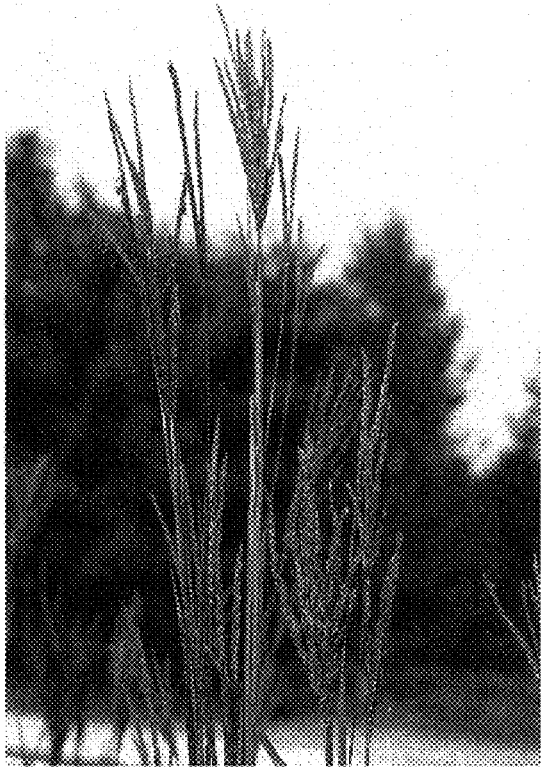
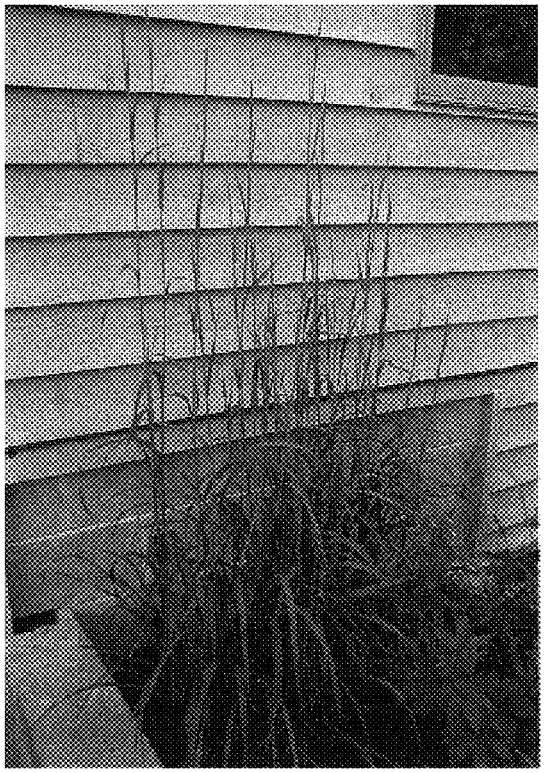

* * * * *